United States Patent [19]

Stano

[11] Patent Number: 5,799,659
[45] Date of Patent: Sep. 1, 1998

[54] ANKLE FOOT ORTHOSIS NIGHT SPLINT WITH ORTHOWEDGE

[76] Inventor: William S. Stano, 220 W. Jefferson St., Boise, Id. 82702

[21] Appl. No.: 792,491

[22] Filed: Jan. 31, 1997

Related U.S. Application Data

[63] Continuation-in-part of Ser. No. 369,409, Jan. 5, 1995, abandoned.

[51] Int. Cl.[6] ..................................................... A61F 5/37
[52] U.S. Cl. ............................................ 128/882; 602/27
[58] Field of Search .................................. 128/945, 846, 128/882; 602/5, 23, 26, 27, 28, 29

[56] References Cited

U.S. PATENT DOCUMENTS

| | | | |
|---|---|---|---|
| 1,114,389 | 10/1914 | Semeleder | 602/27 |
| 1,396,323 | 11/1921 | Dunne | |
| 1,575,042 | 3/1926 | Denniston | |
| 2,395,936 | 3/1946 | Oleisky | 128/80 |
| 3,814,088 | 6/1974 | Raymond | 128/87 R |
| 4,325,380 | 4/1982 | Malkin | 128/581 |
| 4,351,324 | 9/1982 | Bronkhorst | 128/80 J |
| 4,369,588 | 1/1983 | Berguer | 128/882 |
| 4,378,793 | 4/1983 | Mauldin et al. | 128/80 H |
| 4,449,264 | 5/1984 | Schwartz | 12/1 R |
| 4,454,618 | 6/1984 | Curchod | 12/1 R |
| 4,510,636 | 4/1985 | Phillips | 12/1 R |
| 4,517,696 | 5/1985 | Schartz | 12/1 R |
| 4,572,169 | 2/1986 | Mauldin et al. | 128/80 H |
| 4,718,179 | 1/1988 | Brown | 36/44 |
| 4,869,001 | 9/1989 | Brown | 36/115 |
| 4,876,758 | 10/1989 | Rolloff et al. | 12/142 N |
| 4,982,733 | 1/1991 | Broadhurst et al. | 128/804 |
| 5,020,523 | 6/1991 | Bodine | 128/882 |
| 5,038,762 | 8/1991 | Hess et al. | 128/80 H |
| 5,224,925 | 7/1993 | Varn | 602/28 |
| 5,298,013 | 3/1994 | Lonardo | 128/882 |

OTHER PUBLICATIONS

The Use of Night Splints for Treatment of Recalcitrant Plantar Fasciitis, Wapner and Sharkey, Foot and Ankle vol. 12, No. 3, Dec. 1991.

*Primary Examiner*—Micheal A. Brown
*Attorney, Agent, or Firm*—Frank J. Dykas

[57] ABSTRACT

A low cost orthosis for the treatment of foot and ankle conditions including plantar fasciitis and tendonitis, the orthosis is a rigid, molded shell manufactured in a variety of incremental sizes, having a generally U-shaped cross-sectional configuration and a flat foot bed, covered by a soft fabric covering, and using a removable and interchangeable foot bed wedge insert permitting the angle of dorsiflexion, plantarflexion, inversion and eversion to be varied.

18 Claims, 9 Drawing Sheets

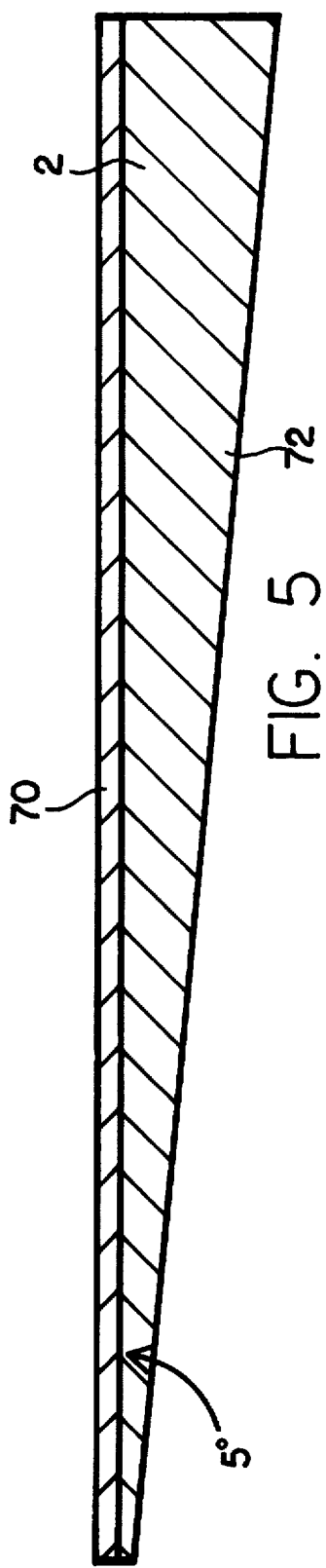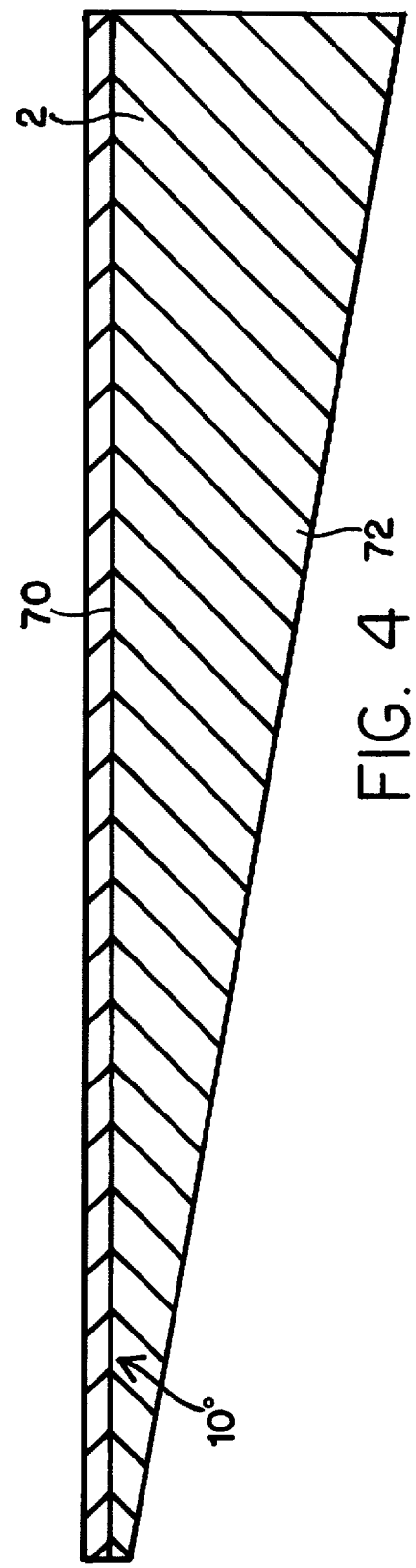

ANKLE FOOT ORTHOSIS NIGHT SPLINT WITH ORTHOWEDGE

This is a continuation-in-part of application No. 08/369,409, filed Jan. 5, 1995, now abandoned.

BACKGROUND OF THE INVENTION

1. Technical Field

The present invention relates to an orthotic device, specifically a night splint for treating and facilitating in the treatment of the pain in the foot and heel caused by contracture of the plantar fascia and or the Achilles tendon, treatment of hip ailments, and post-surgery treatment of the foot.

2. Background

Simply put, the human foot takes the brunt and the impact of every step experienced by an individual. It is also likely that the single largest source of complaint for foot ailments is related to heel pain. One source of heel pain commonly observed is due to a condition known as recalcitrant plantar fasciitis. Plantar fasciitis occurs in the plantar fascia, a fibrous membrane disposed longitudinally across the bottom of the foot. The plantar fascia is attached at the heel bone, more specifically to the inner tubercle of the os calcis. The plantar fascia becomes broader and thinner as it extends longitudinally across the bottom of the foot, eventually dividing near the heads of the metatarsal bones into five processes, one for each of the five toes.

The strongest ligament in the body is the plantar fascia, a fibrous band of tissue that starts on the bottom surface of the heel bone and extends forward on the bottom of the foot to just behind the toes. Its function is to protect the softer muscles and tissues of the bottom of the foot from injury, as well as to help maintain the integrity of the foot structure itself. If the fascia becomes stretched or strained, the arch area becomes tender and swollen as well as about the heel bone. This inflammation is called plantar fasciitis and is painful from the heel throughout the arch up into the Achilles tendon. These patients usually have tight and inflexible heel cords, or what we call Achilles tendon tightness. When the heel cord is tight, it causes compensation in the foot with over pronation of the foot during weight bearing. The pain is consistently worse when you first get up in the morning and at the end of the day. The pain usually lurks in the heel pad and may include the arch ligament. The natural tendency is to ignore the symptoms of the pain at first.

Heel pain like plantar fasciitis is often times caused by contracture of the Achilles tendon and the plantar fascia, which can occur at night during sleep, or during daytime inactivity. The Achilles tendon is the strongest and thickest tendon in the human body. The Achilles tendon begins at or about the middle of the posterior side of the leg extending downward towards the heel, narrowing as it progresses towards its point of insertion at the posterior surface of the os calcis. When an individual is standing, walking, running or even sitting in a position in which the feet are in contact with the floor or other surface, both the plantar facia and the Achilles tendon are extended to varying degrees depending of course on the nature and intensity of the activity. During sleep, an individual has a natural tendency to plantarflex the ankle joint beyond the position which is normal during walking, standing or sitting with one's feet on the floor. Plantar flexion is when the bottom of the foot is extended so as to form an angle with the lower leg of greater than 90°. Dorsiflexion is the opposite motion, when the foot is moved to a position in which the bottom of the foot forms an angle with the lower leg of less than 90°. As a result of plantar flexion during the night, the plantar facia and the Achilles tendon contract from their size and dimension normal to the walking, standing or sitting positions. Upon arising, the plantar facia and the Achilles tendon are once again extended and stretched when the feet and ankles resume a normal position associated with walking or standing. Typically, it is when an individual arises following sleep or a period of extended recumbency that the effects of heel pain associated with plantar faciitis, with or without the associated Achilles tendon contracture, are observed, and in a significant number of cases the pain has been described as substantial.

Various theories explain the constant pull of the plantar fascia at the insertion of the heel bone. The plantar fascia and intrinsic muscles can cause spurs or tearing of the fascia at the insertion. With continued pull, subperiosteal bleeding can produce calcification leading to new bone. Other theories are constant stress of the fascia with excessive stress at the insertion forming new connective tissue with the tissue going from fibrocartilaginous tissue to cartilaginous to bone. A reference to the thickening of the plantar ligaments is found as early as 1859 in a dissection of a flat foot by Dr. Wood.

In various types of occupations, sedentary work may produce atrophy and degeneration of the shock absorption ability of the heel's fat pad. Occupations which produce over-use of tissue which is stressed beyond its physiologic limits such as working at a factory machine or the static loading exposure of welding may also cause fat pad atrophy and degeneration from long, unnatural hours of standing on hard surfaces owing to the degeneration of the plantar fascia.

Plantar fasciitis is a condition characterized by tenderness located at or near the point at which the plantar fascia attaches to the heel bone, or the os calcis. This condition has been traditionally treated in a number of ways including non-steroidal anti-inflammatory medicines, cortisone injections, shoe modifications, physical therapy and even surgery.

It is referred to in a book in 1915 by Dr. Scholl as policeman's heel. Reference can be found in literature on heel pain before 1900. Authors writing about the conditions affecting the foot referenced it as pain of various courses from systemic disease to pain related to the plantar fascia. In 1860, Zacharie discussed a condition affecting the heel in which patients had greater pain in the morning than after standing and walking for one or two hours. In 1900, Plettner noticed inferior heel spurs on patients' radiographs. After that many theories were put forth on the cause of heel pain and plantar fasciitis and the amount of references in the literature had more prevalence in this time. In 1915, Dr. Scholl indicated that painful heel pain was usually accompanied by flat foot, giving us the revelation that was correlation between pronation and painful heels.

The earliest records reviewed found treatment for heel pain was in a 1915 article by Waechter and Sonnenschein in which they used felt aperture pads for the treatment of painful heel pain. Dr. Scholl in 1915 advocated the use of a metal orthotic called the Trispring. Metal was placed into the arch to support it and prevent elongation of the arch and a leather top was applied over the metal. Dr. Carl Bergman states that in his orthopedic lecture notes taken at the Illinois College of Chiropody in 1919 suggests the use of a sponge heel pad in the shoe for the local relief of heel pain.

Favorable results for the treatment of plantar fasciitis were observed in a recent study which employed night splints in connection with other non-surgical therapeutic measures in treating this condition. See Wapner and Sharkey, THE USE OF NIGHT SPLINTS FOR TREATMENT OF RECALCITRANT PLANTAR FASCITIS, Foot and Ankle Vol. 12, No. 3, Dec., 1991. The night splint consists, essentially, of a boot-like structure which is strapped to a patient's lower leg and foot, holding the foot relative to the lower leg in a position such that the ankle joint is held in slight dorsiflexion. In so doing, both the plantar fascia and the Achilles tendon are slightly extended and are not allowed to contract during the night. The use of night splints together with the variety of other elements of treatment including anti-inflammatory medications, physical therapy and foot cushions for use during the daytime, has proved beneficial in the treatment of plantar fasciitis.

It is desirable to have an orthosis which has the possibility of inducing inversion or eversion of a patient's foot. Inversion is when the bottom of the foot, the plantar surface, faces more toward the midline of the body. Eversion is motion of the foot in which the plantar surface of the foot is tilted so as to face further away from the midline of the body.

The splints described in the Wapner-Sharkey article consisted of a custom molded ankle-foot orthosis constructed of polypropylene. The authors of that article approximate the cost of each splint at $200.00. See Wapner/Sharkey at pages 135, 136.

It is suggested that the relatively high price of the splints used in the Wapner/Sharkey study is due in part to the custom molding required to form the splint to conform to the patient's anatomy. Additionally, a custom molded orthosis can be used by only one patient.

Various other splints are advertised for treatment of plantar fasciitis which also typically consist of a molded splint or a combination of molded plastic and metal framework, with the dorsiflexion set at 5 degrees.

Although similar in appearance to foot and ankle casts, also called walking casts, a night splint for the treatment of plantar fasciitis is only superficially similar to a walking cast. A foot or ankle cast is made so that the force vector of the patient's weight passes vertically through the cast and the patient's leg when he is standing. In the medical industry, no walking casts are made which do not place the bottom of the patient's foot at a 90° angle to the patients leg, which is consistent with a vertical force vector. Thus, no walking casts are built to induce and maintain dorsiflexion or plantar flexion. In addition, a walking cast is made to provide the patient with a weight-bearing region forward of the heel, on which the weight of the body is placed when walking, and from which the patient can pivot forward when taking the next stride. The bearing and pivoting structure can be a rounded knob under the mid region of the foot, or it can be a rounded surface which covers the bottom of the cast from heel to toe. A walking cast may also have a cushioning region directly under the heel to absorb some of the shock of walking. Walking casts are not made to wear in bed at night, and are not made to induce a stretching effect on tendons. They are made to provide support to healing ankle and foot joints and bones, and to control the motion of these healing joints and bones while healing takes place.

To treat plantar fasciitis, it is necessary to use considerable force to counteract the strong muscles and tendons of the lower leg and foot. If this force is applied improperly, pressure points can result, with resulting discomfort and complications for some patients. Some patients have reduced blood circulation or sensation in the feet, such as patients with diabetes, vascular insufficiency, polio, stroke, trauma, or neurological problems. In such patients, if they need to use a night splint for treatment of plantar fasciitis, it is important to minimize the pressure points exerted by the night splint on the patient's foot, while still exerting the necessary force on the foot and lower leg structure. The night splint must also not bruise or scratch the collateral leg during sleep, must not soil or tear bedding, and must be compatible with a sleeping partner. Walking casts are not designed to accomplish these objects.

Another ailment for which a night splint is needed is calcaneal apophysitis. This is typically a problem which presents in juveniles. It is basically a case of the bones of the leg and foot growing faster than the connective tissue, such as the plantar fascia and Achilles tendon, and the heel bone is immature and somewhat soft. These two tendons are put under strain, and cause heel pain. Treatment of calcaneal apophysitis has proven to be very successful using a night splint. The night splint prevents foot drop during sleep, and helps lengthen the two involved tendons.

Paratendon tendonitis is another condition for which a night splint is needed for successful treatment. The partendon is a thin sheathlike covering of tendons. The lining of this structure can become inflamed, and require night-time stabilization to immobilize the foot and lower leg and treatment.

Achilles tendonitis is another condition for which a night splint is needed for successful treatment. Achilles tendonitis can result from overuse of the tendon in sports activities, and can also result from a number of inflammatory diseases, of which rheumatoid arthritis is one. Use of a night splint is an effective treatment for this ailment, since immobilizing the Achilles tendon without allowing night drop or contracture of the tendon is the best treatment.

Another area where a night splint is needed is after various surgeries on the hip. After hip replacement, for instance, it is desired that the involved hip joint remain absolutely immobile. What is needed is a device which immobilizes one or both feet and lower legs, so that the hip joint is not moved.

Another situation which requires the use of a night splint is when surgery has been performed on tendons in the foot. If the tendons worked on are on the medial side of the foot, it is desirable for the foot to be held in an inverted position (with the plantar surface facing toward the midline of the body). This relieves strain on the affected tendons. If the tendons worked on are on the lateral side of the foot, an everted position is desirable.

Accordingly, it is an object of the invention to provide an orthosis which is suitable for use on a patient's foot and lower leg during the night, as a night splint for the treatment of plantar fasciitis, Achilles tendon problems, hip immobilization, and post-surgery treatment of the foot. The orthosis needs to hold the foot in a generally dorsiflexed position with adjustments available for holding the plantar surface of the foot from 90° to 75° from the longitudinal axis of the lower leg.

It is also an object of the invention to provide an orthosis which secures the foot in a dorsiflexed position, and which secures the heel in a floating heel cup.

It is another object of the invention to provide an orthosis which is anatomically designed to be close fitting, in order to provide support and to reduce pressure points.

It is a further object of the present invention to provide a splint or orthosis which may be employed in treating plantar fasciitis, contractures of the Achilles tendon and other tendinous structures of the foot, such as the flexor tendons for the feet and ankles which would be lower in cost and more versatile than the presently available alternatives.

It is also an objective of the present invention to provide an orthosis having removable and interchangeable foot bed wedge inserts which will permit the angle of dorsiflexion to be varied, as well as the angle of inversion and eversion, allowing certain therapeutic advantages. Additionally, the ankle joint may be extended beyond the neutral position, (dorsiextension) or rotated medially or laterally, for other various therapeutic uses merely by substituting foot bed inserts.

Finally, an objective of the present invention is to provide a low cost orthosis which consists of a molded shell which is manufactured in a variety of incremental sizes, i.e. extra small, small, medium, large and extra large, which may be used by a variety of patients obviating the need for custom molding.

DISCLOSURE OF INVENTION

According to the present invention, the foregoing and other objects and advantages are attained by a device for treating plantar fasciitis which includes a rigid shell member which has an upper section and a lower section. Both sections are generally U-shaped in cross-section. The lower section extends at an angle of less than 90° from the upper section. The lower section has a generally flat foot bed portion. The upper section is configured to generally conform to the lower portion of the human leg, and the lower section is configured to receive a bottom surface of a foot attached to a human leg. A removable wedge foot bed insert is included as part of the device and it is configured to be received in the foot bed portion of the lower shell section. The wedge is typically inclined from a heel portion to a toe portion and thus forms an inclined foot bed which prevents plantar flexion and promotes dorsiflexion. A securing mechanism is also included as part of the device and is used to secure a patient's foot in the device for treating plantar fasciitis. The securing mechanism is flexible in at least an area above the foot bed to allow for adjustable degrees of dorsiflexion while preventing plantar flexion past the fixed angle of the inclined foot bed.

Removable wedge foot bed insert results in a foot bed which is less than 90° in relation to the upper shell section. An angle between 75° and less than 90° has been found to be an optimal range. The device for treating plantar fasciitis can be made from a variety of sizes of rigid shell members. The sizes correspond to U.S. shoe sizes, as described in the Best Mode section. It is important that the correct size be selected so that the shape of the device is properly proportioned to the length of a person's lower leg. By properly sizing the device, the heel can be secured in a floating position so that it does not touch the foot bed. This device can also be configured with a removable wedge foot bed insert which is higher on one side of the removable wedge foot bed insert than on the other side. This results in inversion or eversion of the patient's foot when placed in the device. A range of greater than 0° and inclusive of 15° has been found to be an optimal range for inversion or eversion.

Another aspect of the invention is a method for treating plantar fasciitis. The method consists of securing a rigid shell to the lower posterior portion of the leg and foot of a patient. The rigid shell has an upper section and a lower section, with both sections having generally U-shaped cross-sections. The lower section extends at an angle of less than 90° from the upper section and has a generally flat foot bed portion. The upper section is configured to generally conform to the lower portion of a human leg and the lower section is configured to receive a bottom surface of a foot attached to that leg. The method also includes inserting a removable wedge foot bed insert which is inclined from a heel portion of a foot bed to a toe portion of the foot bed, and which forms an inclined foot bed in the lower shell section. This inclined foot bed prevents plantar flexion of the foot, and induces dorsiflexion of the foot. The rigid shell secured to the leg and foot by means of a securing mechanism which is flexible in at least an area above the foot bed to allow for adjustable degrees of dorsiflexion while preventing plantar flexion past the inclined foot bed.

Another aspect of the invention is a method for treating plantar fasciitis whose steps include inserting a removable wedge into a foot bed portion of a rigid shell which has an upper and a lower section. Both the upper and the lower section have a generally U-shaped cross-section. The lower section extends at an angle of less than 90° from the upper section and has a generally flat foot bed portion. The upper section is designed to generally conform to the lower portion of a human leg. The lower section is designed to receive a bottom surface of the patient's foot. The wedge is also configured to receive a bottom surface of a foot, and is inclined from a heel portion to a toe portion. The wedge, therefore, forms an inclined foot bed which prevents plantar flexion. Another step in the method is securing the shell to the lower posterior portion of a leg and foot of a patient using a securing mechanism which is flexible in at least an area above the foot bed to allow for adjustable degrees of dorsiflexion while preventing plantar flexion past the inclined foot bed.

Another aspect of the invention is an orthosis which includes a rigid shell member with an upper and lower section. Both the upper and lower sections have a generally U-shaped cross-section. The lower section has a heel portion and a toe portion, and extend at an angle of less than 90° from the upper section. The lower section has a generally flat foot bed portion, with the heel portion narrower than the toe portion and designed for close anatomical fit with the heel of a human patient. The upper section is configured for close and anatomically conforming shape to the lower posterior portion of the human leg, and includes a sagitall concavity which conforms to the human leg and maintains the human heel in a floated position from the flat foot bed. This floated position of the heel is achieved by securing the leg in the rigid shell member against the sagitall concavity. The upper shell section is proportioned to be considerably longer than the lower shell section. The upper shell section is of a length which corresponds with the distance from the patient's heel to above the thickest portion of the gastroxcelius muscle. The length of this section of the rigid shell member is designed to provide optimal support to the leg and muscles involved and to reduce pressure points. The lower shell section is configured to be about the same length as the foot of the patient. Typically, the upper shell section is about twice as long as the lower shell section. The lower shell section is designed to receive a removable wedge foot bed insert. The rigid shell member is shaped so that two openings are defined and in which the ankle bones of the patient are placed when the device is attached. In this way, the rigid shell member leaves the ankle bones of the user free and their only contact is with the fabric covering of the rigid shell member. This configuration of the device also includes a removable wedge foot bed insert which is typically inclined from a heel portion to a toe portion of the foot bed. It therefore forms an inclined foot bed which prevents plantar flexion of the foot. The removable wedge foot bed has a cushioning top surface which is soft and flexible, and it also contains a semi-rigid material to which the cushioning top surface is attached. The device also includes a soft jacket which covers the inside and outside surfaces of the rigid shell and to which is attached a securing means. The securing means is flexible in at least an area above the foot bed to allow for adjustable degrees of dorsiflexion while preventing plantar flexion past the inclined foot bed. Removable wedge foot bed inserts can be designed to result in a foot bed of from less than 90° to 75°.

In another aspect of the invention, the invention consists of a method for treating plantar fasciitis in a human patient which includes the steps of inserting a removable wedge into a foot bed portion of a rigid shell having an upper and a lower section, both sections generally having a generally U-shaped cross-section, the lower section having a heel portion and a toe portion, and being narrower in the heel portion than in the toe portion, to facilitate a close anatomical fit to a human foot. The lower portion extends at an angle of less than 90° from the upper section and has a generally flat foot bed portion. The upper section is designed for close anatomical conformance to the lower portion of a human leg. When worn by a patient, the upper section extends from the heel of the patient above the thickest part of the patient's gastroxcilius muscle. The rigid shell is covered with a soft covering on its inside and outside surface. The wedge is typically inclined from a heel portion of the foot bed to a toe portion of the foot bed, and thus forms an inclined foot bed which prevents plantar flexion. Another step of the method is securing the rigid shell to the lower posterior portion of a leg and foot using a securing mechanism which is flexible in at least an area above the foot bed to allow for adjustable degrees of dorsi flexion while preventing plantar flexion past the inclined foot bed. Another step is requiring the patient to wear the rigid shell, the soft covering and the wedge, secured by a securing mechanism to the lower posterior portion of the leg and the foot, while in a reclining position which can occur during sleep or at other times.

In another aspect of the invention, the invention is a method for preventing hip movement in a human patient and includes the steps of securing the rigid shell to the lower limp limb of a patient, the rigid shell having an inner and an outer surface and an upper section and a lower section. Both sections have generally U-shaped cross-sectional shapes. The lower section includes a heel portion and a toe portion, the heel portion being narrower than the toe portion for close anatomical fit to a human foot. The lower section extends at an angle approximately at an angle of less than 90° from the upper section and has a generally flat foot bed portion. The upper section is designed for close anatomical conformance to a lower portion of a human leg, and when worn by a patient extends from the heel of a patient to above the thickest part of the patient's gastroxcilius muscle. The lower section is configured to receive a bottom surface of the patient's foot. The rigid shell is covered with a soft covering on at least its inside surface and may be covered on its outside surface in addition. The next step in the process is securing the rigid shell to the lower posterior portion of the leg and foot of a human patient, using a securing mechanism which is flexible in at least an area above the foot bed to allow for adjustable degrees of dorsiflexion while preventing plantar flexion past the inclined foot bed. Another step in the method is placing the rigid shell with the leg and foot of a patient in a stabilizing cradle and securing the rigid shell in a fixed position in the stabilizing cradle with a means of attachment. This means of attachment can be Velcro® straps or hook and loop fasteners, or other conventional means of securement. The next step of the method is requiring the patient to wear the rigid shell and the soft covering, secured by the securing mechanism to the lower posterior portion of the leg and the foot and the rigid shell attached to the stabilizing cradle with a means of attachment while in a reclining position. Optionally, a wedge may be used in the orthosis.

The method and apparatus of the invention, using a rigid shell which holds the foot at an angle of less than 90° to the leg, thus prevents plantar flexion of the foot and promotes dorsi flexion of the foot without applying pressure to the heel. The orthosis can also be used for post surgery treatment of a foot, leg and hip, to relieve pressure on the area which has been operated on, and to immobile areas requiring such immobilization.

Still other objects and advantages of the present invention will become readily apparent to those skilled in this art from the following detailed description, wherein I have shown and described only the preferred embodiment of the invention, simply by way of illustration of the best mode contemplated by me of carrying out my invention. As will be realized, the invention is capable of modifications in various obvious respects, all without departing from the invention. Accordingly, the drawings and description are to be regarded as illustrative in nature, and not as restrictive.

BRIEF DESCRIPTION OF THE DRAWINGS

FIG. 4 is a side plan view of a 10 degree removable foot bed wedge insert.

FIG. 5 is a side plan view of a 5 degree removable foot bed wedge insert.

BEST MODE FOR CARRYING OUT INVENTION

Figure 1:
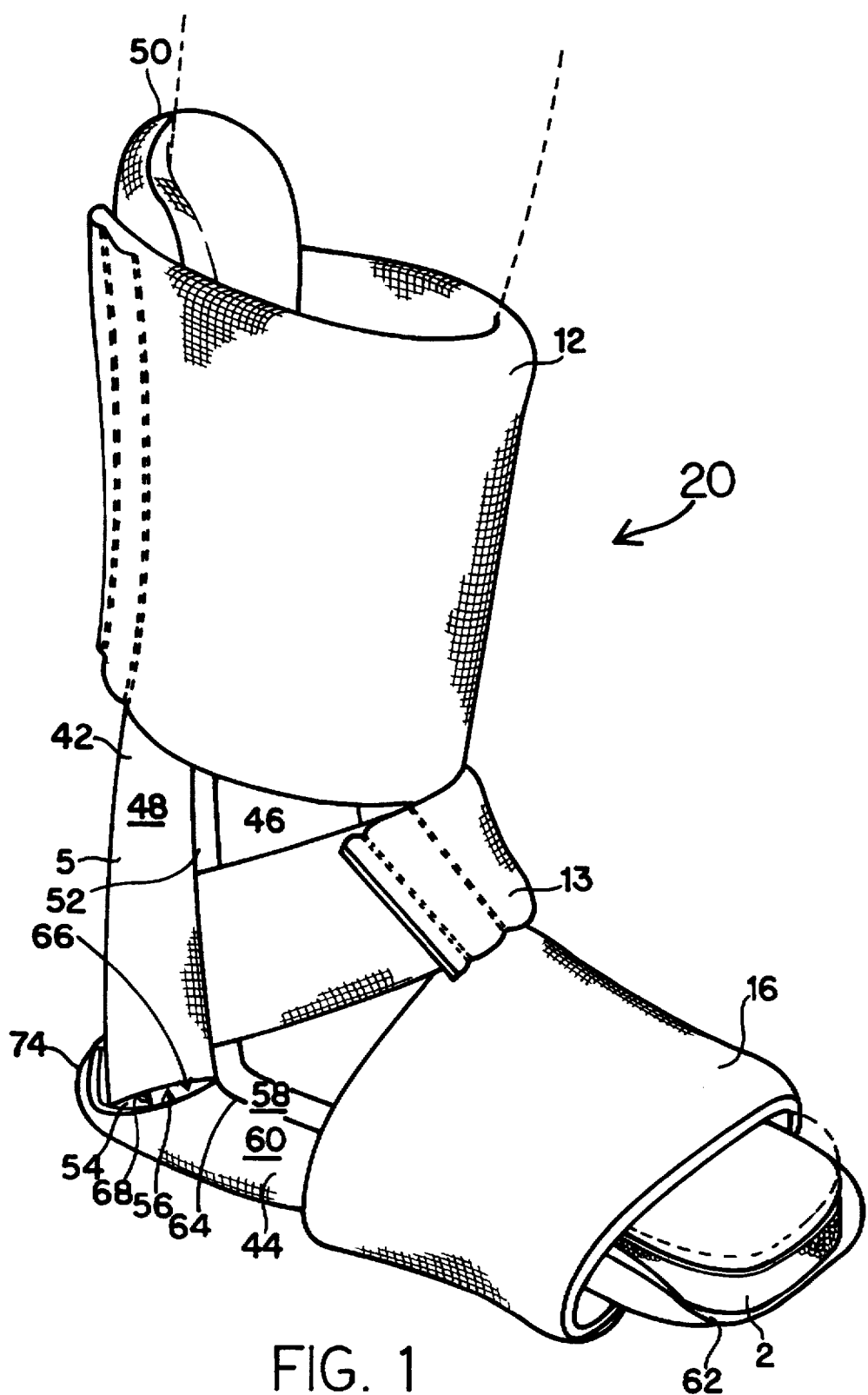
FIG. 1 is a perspective view showing the ankle foot orthosis.
Figure 2:
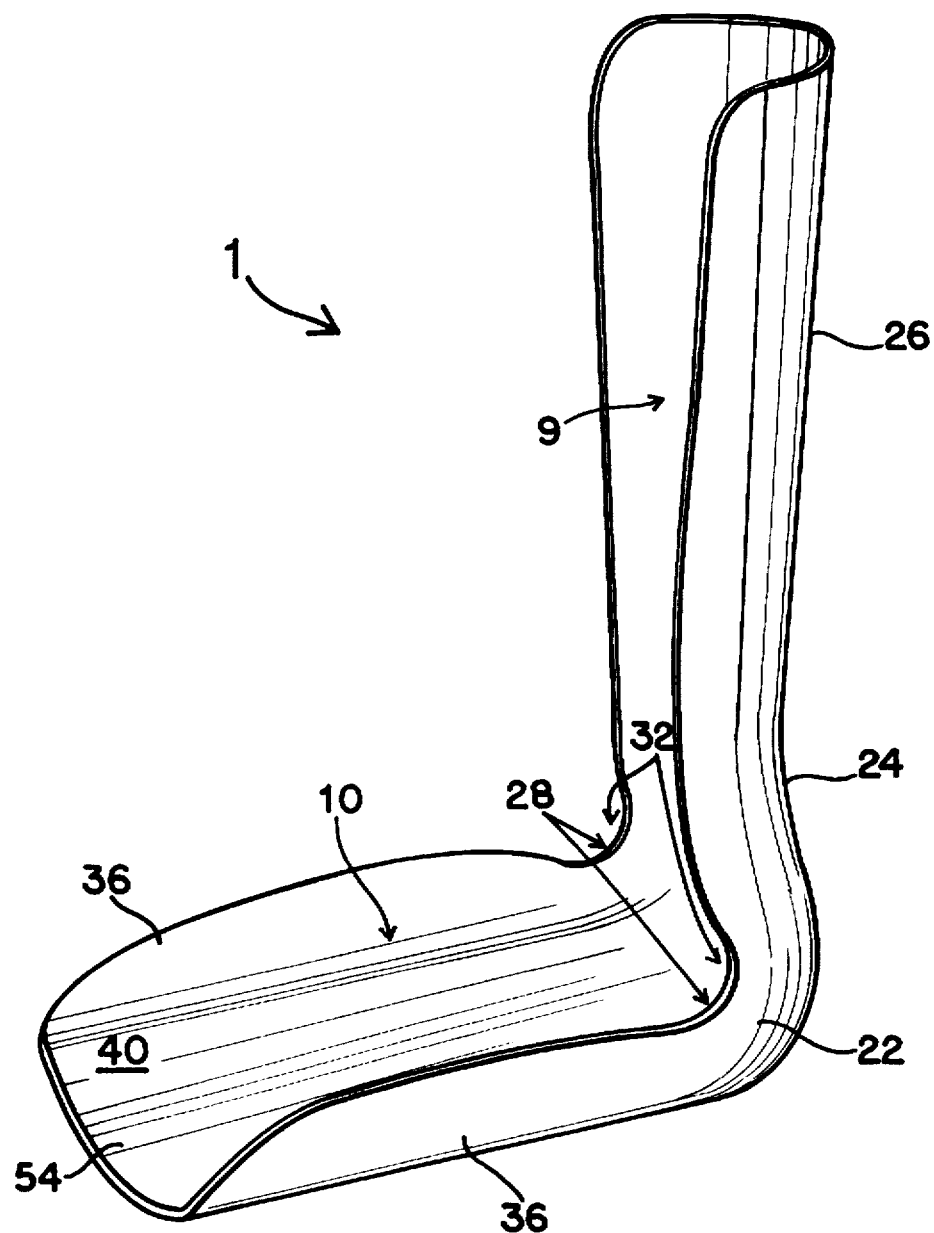
FIG. 2 is a perspective representational view of the rigid shell.
Figure 3:
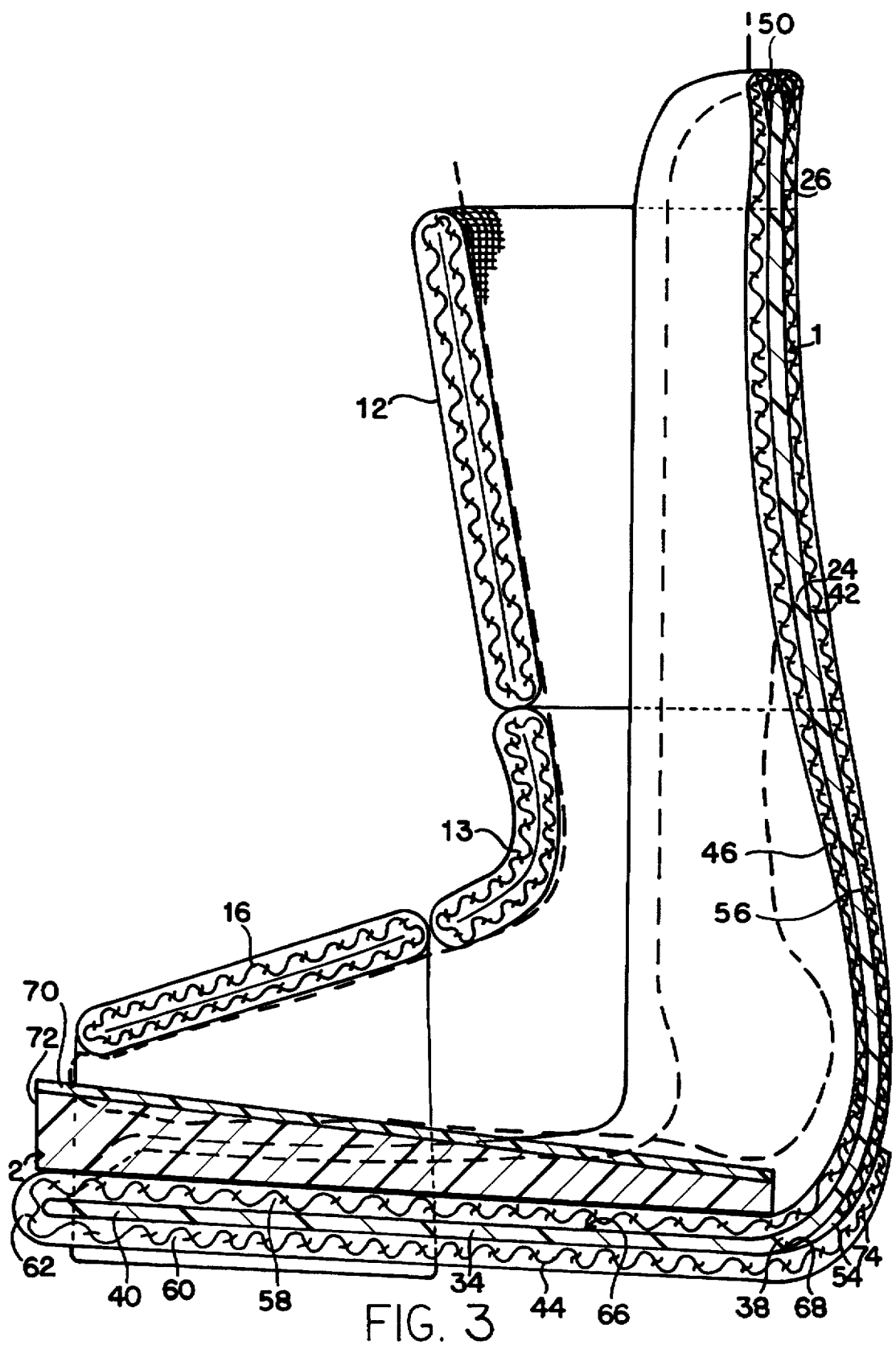
FIG. 3 is a cut-away side plan view of the ankle foot orthosis.

Referring to FIGS. 1 through 5, 8 and 11, the ankle foot orthosis is shown to advantage. FIG. 1 shows the ankle foot orthosis 20 secured to a lower leg LL and foot F of a patient. As shown in FIGS. 1, 2, and 3, ankle foot orthosis 20 consists of a rigid shell member 1, a fabric covering 5, and a removable wedge foot bed insert 2. The fabric covering 5 also includes lower leg attachment strap 12, instep attachment strap 13, and foot attachment strap 14. The fabric covering 5 surrounds and covers the inside surface and the outside surface of rigid shell member 1 of the ankle foot orthosis 20.

Rigid shell member 5 consists of an upper shell section 9, and a lower shell section 10. The two are attached to each other, and in the best mode the rigid shell member 5 is made from one piece of plastic, although other materials could be utilized. In the preferred mode, lower shell section 10 extends from upper shell section 9 at an angle of approximately 80°. Upper shell section 9 and lower shell section 10 each have a cross-sectional shape which is generally U-shaped.

Upper shell section 9 is shaped to closely follow the contours of the posterior of a patient's foot and lower leg. It therefore has a heel pocket 22, a sagittal concavity 24, and a calf flare 26, as shown in FIG. 3. Calf flare 26 is designed to extend beyond the thickest portion of the patient's gastroc-soleous muscle. Where upper shell section 9 joins lower shell section 10, ankle flares 28 provide room for the orthosis 20 to extend around the ankle protrusions of the patient. Ankle sockets 32 define a region which surrounds the ankle bones of the patient. The shape of the ankle flares 28 allow the rigid shell member 1 to flex so that the upper shell section 9 and the lower shell section 10 approach each other, in a dorsiflexion direction, but does not allow them to move away from each other in a plantar flexion direction.

Lower shell section 10 has a flat foot bed 34, side pieces 36, and joins upper shell section 9 at the heel pocket 22 and the ankle sockets 32. Flat foot bed 34 has a heel portion 38 and a toe portion 40. Flat foot bed 34 is narrower at the heel portion 38 than at the toe portion 40, to accommodate the typical contour of a human foot F.

Fabric covering 5 includes an upper section 42 and a lower section 44. In the preferred mode, fabric covering 5 is made of a foam lined fabric, but any cushioning material can be utilized. Upper section 42 of fabric covering 5 has an inner layer 46 and an outer layer 48, which are connected to each other along the top edge 50 and the two side edges 52. An inner pocket 56 is accessible through opening 54.

Lower section 44 of fabric covering 5 has an inner layer 58 and an outer layer 60, which are connected to each other along the toe edge 62 and the two side edges 64. An inner pocket 66 is accessible through opening 68. A closing flap 74 on the lower section 44 has a region of hook connectors which binds to the fabric of the upper section 42 of the fabric cover 5.

Fabric covering 5 is provided with a lower leg attachment strap 12, an instep attachment strap 13, and a foot attachment strap 14.

In the preferred mode, removable wedge foot bed insert 2 is composed of two layers of foam, a soft top layer 70 and a firm foam layer 72. In the preferred mode, soft top layer 70 is made of Sentinel Blue F-Cell MTL foam, a crosslinked polyethylene foam, but another soft material could also be utilized. Firm foam layer 72 is preferably Sentinel White MTL F-Cell AW900, a cross-linked polyethylene foam, but other materials could be utilized which provide support and resist deformation. In the preferred mode, removable wedge foot bed insert 2 fits the flat foot bed 34 of the lower shell section 10. This means that removable wedge foot bed insert 2 is narrower at the heel portion 38 than at the toe portion 40. In the preferred embodiment, it is typically thinner at the heel portion 38 than at the toe portion 40, and a variety of foot bed angles can be formed from removable wedge foot bed inserts 2 of varying angles. Other embodiments of the preferred mode may utilize removable foot bed inserts 2 which vary in thickness from one side to another, as will be discussed later.

Ankle foot orthosis 20 is assembled by compressing upper shell section 9 toward lower shell section 10. With the two shell section thus in close proximity, the inner pockets 56 and 66 of fabric covering 5 are slipped over the ends of the upper shell section 9 and lower shell section 10. Closing patch 74 is used to attach the lower section 44 to the upper section 42 of fabric cover 5.

Ankle foot orthosis 20 is secured to the lower leg LL of a patient by lower leg attachment strap 12 which passes across the lower leg and attaches by hook fasteners to the fabric on the opposite side of the fabric covering 5. Instep attachment strap 13 passes similarly across the instep of the patient's foot F and attaches to the fabric cover 5 opposite the strap. The lower section of the ankle foot orthosis 20, that portion which surrounds and encloses the foot, is secured and closure is effected by foot attachment strap 16, and a similar hook fastener which attaches to the fabric of the fabric covering. Other means of fastening can be utilized, such as the use of straps and buckles, metal loops to pass straps through, and any conventional means of attachment.

Referring to FIG. 3, a cut-away side view of the ankle foot orthosis 20 is shown to advantage. Ankle foot orthosis 20 consists of a rigid shell member 1 having upper shell section 9 and lower shell section 10. In this view, rigid shell member 1 is configured such that it extends up the back side or posterior side of the patient's leg extending down and around the heel, forming a substantially flat foot bed. In the preferred embodiment, rigid shell member 1 is formed of one piece.

FIG. 3 also shows to advantage the inner layer 46 and the outer layer 48 of the upper section 42 of the fabric covering 5, and the inner layer 58 and the outer layer 60 of the lower section 44 the fabric covering 5.

Figure 8:
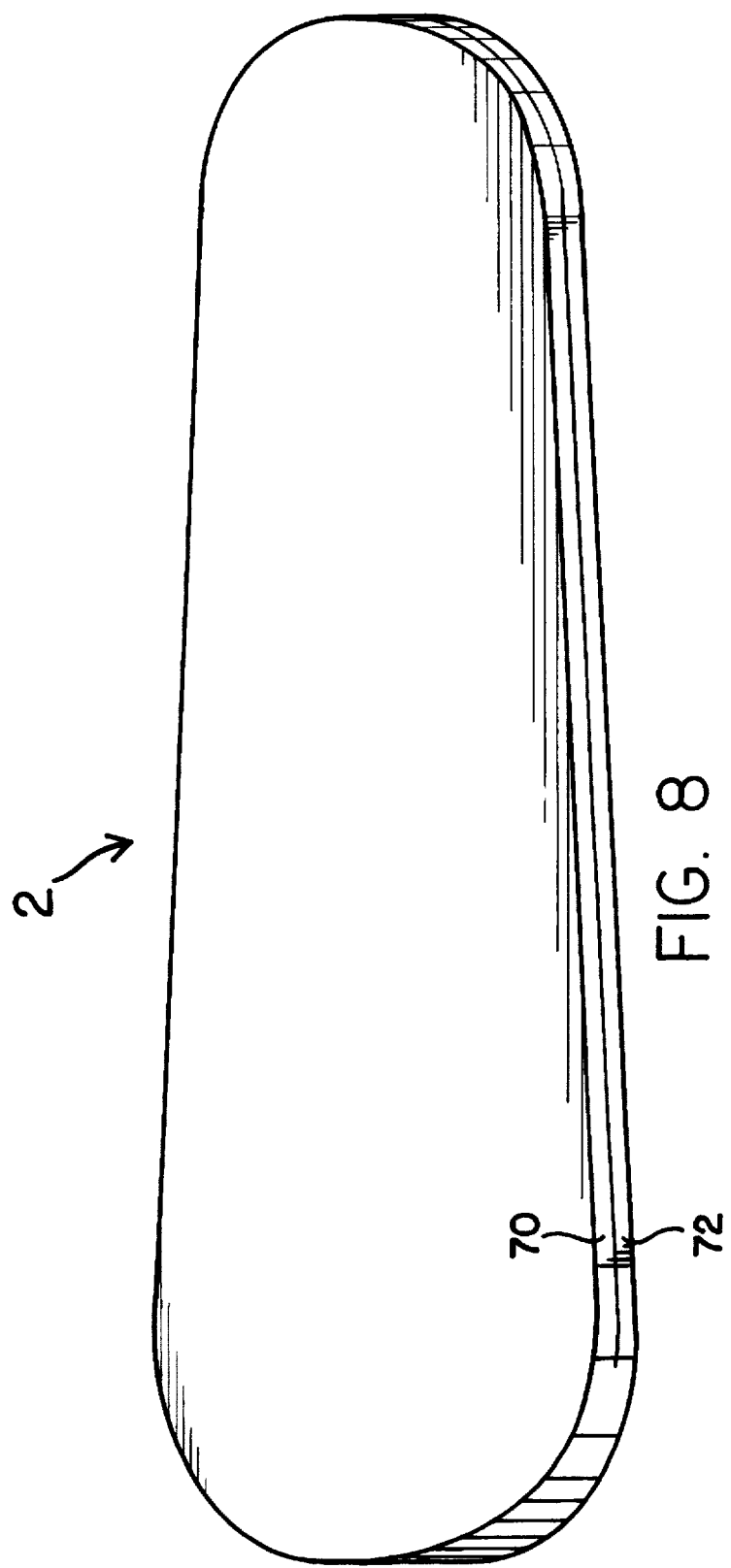
FIG. 8 is a representational view of a removable wedge which when used with the orthosis would result in inversion or eversion of the patient's feet.
Figure 9:
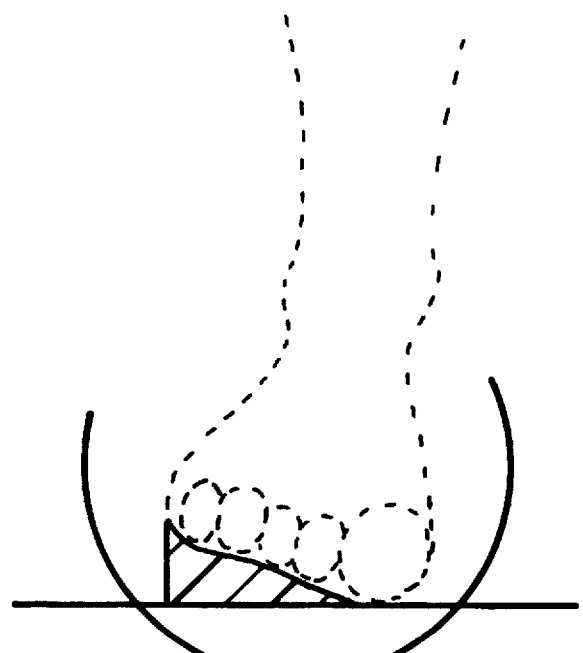
FIG. 9 is a front view of a human foot and a removable foot bed wedge insert in everted configuration.
Figure 10:
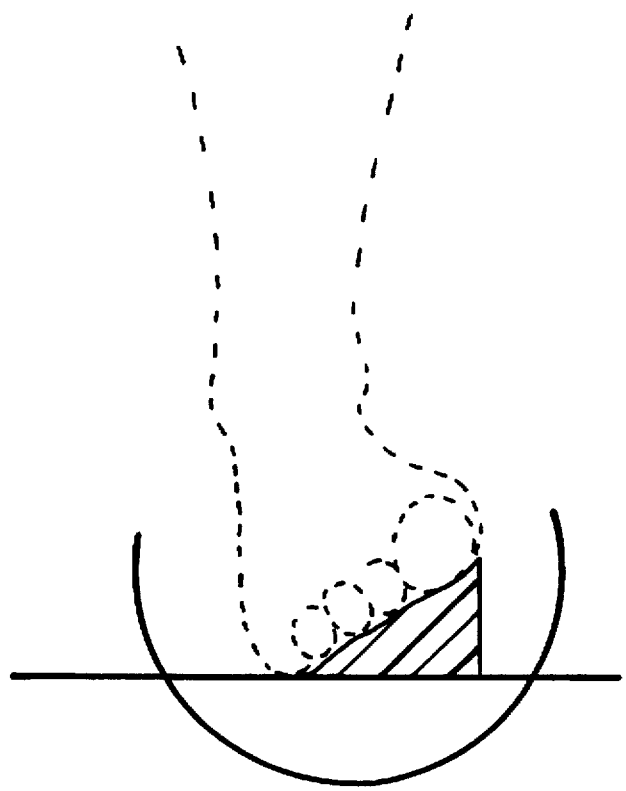
FIG. 10 is a front view of a human foot and a removable foot bed wedge insert in inverted configuration.

Also shown in FIG. 3 is removable wedge foot bed insert 2. Removable wedge foot bed inserts of varying angles can be used to achieve the desired degree of dorsiflexion or plantar flexion of the foot. The removable wedge foot bed insert can also be used to cause inversion or eversion of the foot. To achieve inversion or eversion, the removable wedge foot bed is built as shown in FIG. 8, and is used as shown in FIGS. 9 and 10.

FIGS. 4 and 5 show two variations of removable wedge foot bed inserts 2. FIG. 4 shows a 10° wedge for use with ankle foot orthosis 20 and FIG. 5 shows a 5° wedge for use with ankle foot orthosis 20.

Figure 6:
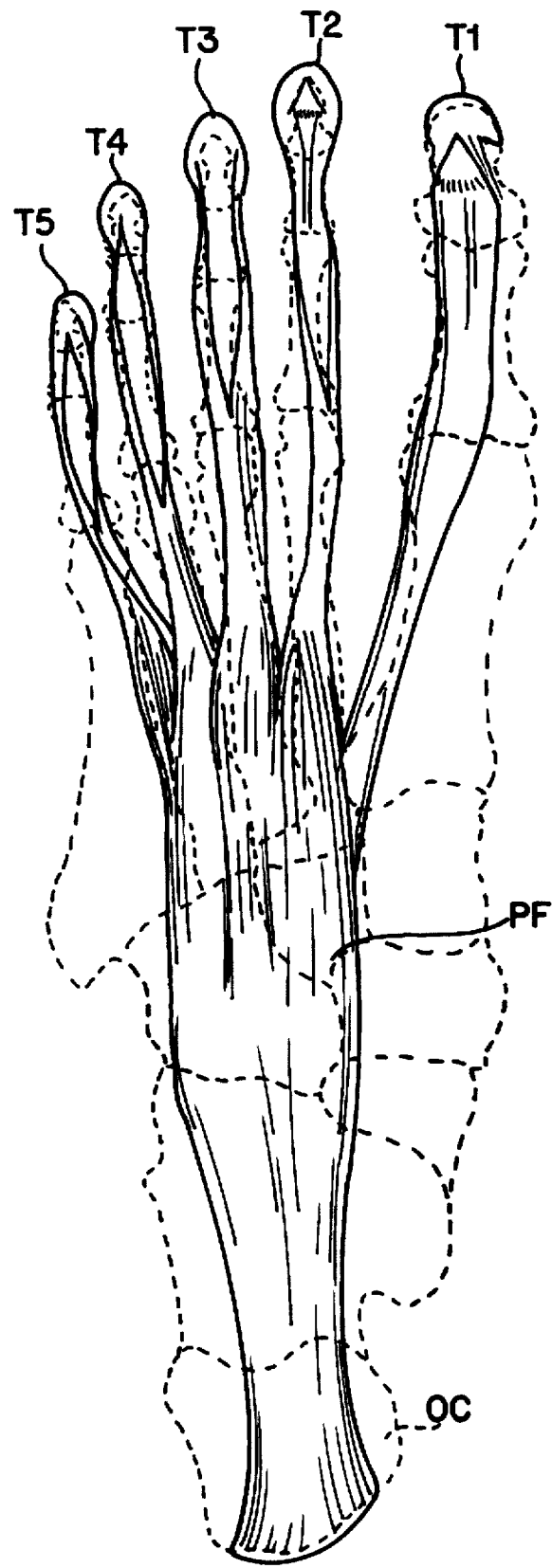
FIG. 6 is a dorsal or bottom anatomical plan view of a human foot.

FIG. 6 shows to advantage a bottom view, or plantar view, of the human foot depicting the plantar facia PF attaching at the heel bone or os calcis, extending longitudinally across the bottom of the foot, eventually dividing near the heads of the metatarsal bones into five processes, one process attaching to each of the five toes, T1 through T5.

Figure 7:
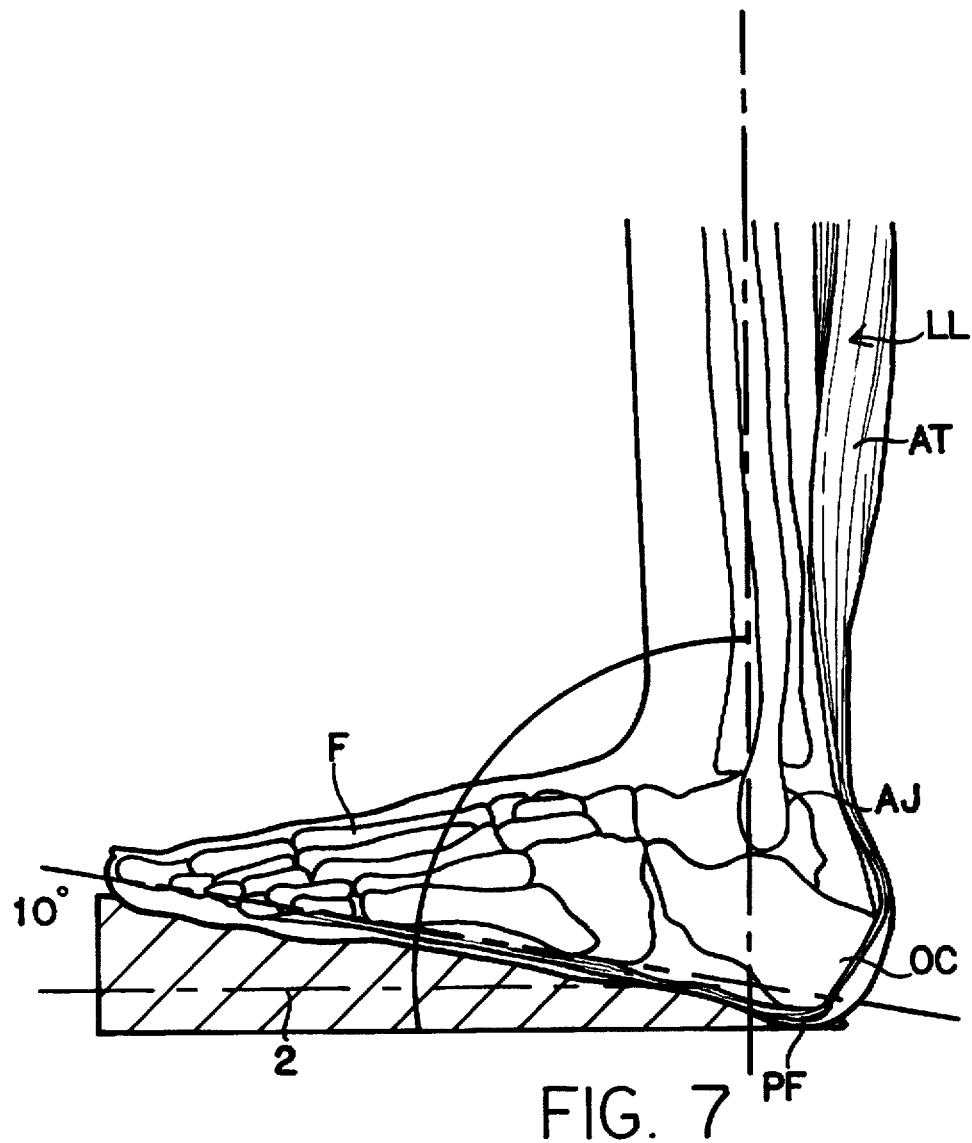
FIG. 7 is a side view of a human foot and a removable foot bed wedge insert.

FIG. 7 shows ankle joint AJ, formed by the articulation of foot F with lower leg LL, specifically the articulation of the tibia and the fibula, the two bones which comprise the skeletal frame of the lower leg and the astragalus, the largest of the tarsal bones located next to the os calcis. FIG. 7 shows ankle joint AJ in 10° dorsiflexion. The dorsiflexion in this instance is caused by removable wedge foot bed insert 2 having a 10° incline. Use of this wedge foot bed results in a foot bed which is 80° in relation to the angle of the upper section of the orthosis.

FIG. 7 also shows the attachment of the plantar facia to the inner tubercle of the os calcis OC and the plantar facia PF extended slightly by the dorsiflexion of the ankle joint AJ. FIG. 7 also shows Achilles tendon AT.

In use, initially, a choice of incremental size of ankle foot orthosis 20 is made selecting a size which most closely conforms to the patient's foot and leg size. The present configuration of ankle foot orthosis has sizes pediatric, small, medium, large, and extra large, which correspond to men's and women's shoe sizes as shown below:

Pediatrics: Women's: smaller than 4

Men's: smaller than 7

Small: Women's: 4–6

Men's: 7–9

Medium: Women's: 6–8

Men's: 9–11

Large: Women's: 8–10

Men's: 11–13

Extra Large: Women's: 11 and larger

Men's: 14 and larger

Next, referring to FIGS. 1 through 7, a removable wedge foot bed insert 2 of a desired angle is chosen and inserted into the foot bed of ankle foot orthosis 20. The chosen wedge can be used to cause dorsiflexion or plantar flexion of the foot, and can also result in inversion or eversion of the foot in relation to the leg. A patient's lower leg LL and foot F are placed into the ankle foot orthosis 20 so that the foot F rests comfortably on the soft top layer 70 of the chosen removable wedge foot bed insert. Lower leg attachment strap 12 is passed from one side of upper shell section 9 to the other side, across the lower leg LL. Similarly, instep attachment strap 13 is secured across the instep and to the fabric of the fabric covering 5 on the opposite side, securing the ankle foot orthosis 20 securely against the instep ankle portion of the individual's anatomy. Foot attachment strap is secured across the patient's foot F. After thus securing the patient's foot, the patient's heel is in a floating position, and is not touching the flat foot bed 34 or the removable wedge foot bed insert 2. This floating heel position is maintained by the shape of the sagittal concavity 24 and the size of orthosis 20 selected for the patient.

The fabric covering 5 of the orthosis 20 is designed to pad the patient's foot from any possible pressure points on the inside of the rigid shell member 1. Additionally, rigid shell member 1 is shaped to minimize any possible pressure points. Fabric covering 5 also protects the collateral leg of the patient from being bumped or bruised by contact with the outside of the ankle foot orthosis 20.

The rigid shell member 1 is designed to closely follow the anatomical contours of the patient's foot, ankle, and lower foot. This serves two purposes: one is to reduce he number of pressure points on the patient's foot. The other is to use the shape of the orthosis to position the patient's heel in a floating position. Since many patients being treated for plantar fasciitis may have tender regions on the heel bone or even bone spurs, it is important that any pressure placed on the foot, ankle and lower leg avoid pressure to the heel, while delivering even and comfortable pressure to other parts of the foot, ankle, and lower leg. Pressure must be applied to the front portion of the foot, but not the heel, so that the foot is pressed and held in a dorsiflexed position during sleep.

When ankle foot orthosis 20 is secured to an individual's lower leg and foot as described hereinabove, the ankle joint is preferably placed in dorsiflexion, but certain condition require the use of plantar flexion, inversion, eversion, or neutral orientation, and these positions are achieved by selecting the pitch of the removable wedge foot bed insert 2 used. A range of dorsiflexion of greater than 0 and inclusive of 15 has proven to be an optimal range for treatment of plantar fasciitis. When the ankle is so flexed, plantar facia PF and Achilles tendon AT are extended and held in a position of extension so long as the ankle foot orthosis 20 is worn as described herein.

Plantar flexion can be preferred after foot or tendon surgery, as an acclimitization to gradual stretching and lengthening of the Achilles tendon and plantar fascia by gradually decreasing plantar flexion and increasing dorsiflexion.

Figure 11:
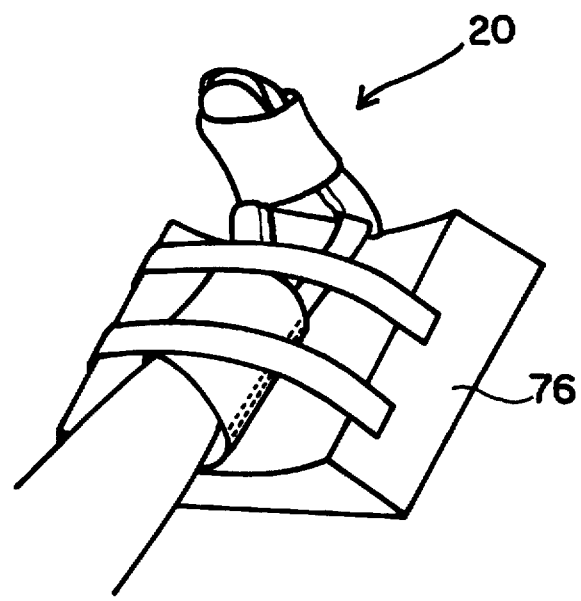
FIG. 11 is a perspective view of an ankle foot orthosis used in conjunction with a stabilizing cradle.

In another preferred embodiment, the ankle foot orthosis is used in conjunction with a stabilizing cradle 76. Stabilizing cradle 76 is a device to which the ankle foot orthosis is attached and secured, as shown in FIG. 11. This mode of operation is indicated for patients recovering from hip replacement surgery or other procedures in which the hip and leg need to be immobilize. With the patient on his back, and one or both legs secured in an ankle foot orthosis 20, which is itself secured to a stabilizing cradle 76, the leg is immobilized and the hip joint can heal optimally.

Inversion or eversion of the foot may also be desired and achieved by the use of appropriately shaped removable wedge foot bed inserts 2. This may occur after surgery on tendons in the foot. If the tendons worked on are on the medial side of the foot, it is desirable for the foot to be held in an inverted position (with the plantar surface facing toward the midline of the body). This relieves strain on the affected tendons. If the tendons worked on are on the lateral side of the foot, an everted position is desirable. A treatment of gradually changing the angle of the wedges from inverted or everted to neutral, and then gradually decreasing the plantar flexion and then increasing the dorsiflexion can be preferred by physicians.

While there is shown and described the present preferred embodiment of the invention, it is to be distinctly understood that this invention is not limited thereto but may be variously embodied to practice within the scope of the following claims.

I claim:

1. A device for treating plantar faciitis which comprises:
   a rigid shell member having an upper section and a lower section, both having generally U-shaped cross-sections, the lower section extending at an angle of less than 90° from the upper section and having a generally flat foot bed portion, the upper section being configured to generally conform to the lower portion of a human leg, and the lower section being configured to receive a bottom surface of a foot attached to the leg;
   a removable wedge foot bed insert being shaped and sized to be received in the foot bed portion, the wedge being inclined from a heel portion of the foot bed to a toe portion of the foot bed to thereby form an inclined foot bed which prevents plantarflexion; and
   a securing mechanism for securing the rigid shell to the lower posterior portion of the leg and the foot, the securing mechanism being flexible in at least an area above the foot bed to allow for adjustable degrees of dorsiflexion while preventing plantarflexion past the inclined foot bed.

2. The device for treating plantar faciitis as described in claim 1, wherein the lower shell section is at an angle of less than 90° to the upper shell section, and the removable wedge foot bed insert results in a foot bed which is less than 90° in relation to the upper shell section.

3. The device for treating plantar faciitis as described in claim 1, wherein the lower shell section is at an angle of less than 90° to the upper shell section and the removable wedge foot bed insert results in a foot bed which is 85° in relation to the upper shell section.

4. The device for treating plantar faciitis as described in claim 1, wherein the lower shell section is at an angle of less than 90° to the upper shell section and the removable wedge foot bed insert results in a foot bed which is 80° in relation to the upper shell section.

5. The device for treating plantar faciitis as described in claim 1, wherein the lower shell section is at a 90° angle in relation to the upper shell section and the removable wedge foot bed insert results in a foot bed which may vary from 90° to 75°0 in relation to the upper shell section.

6. The device for treating plantar faciitis as described in claim 1 wherein the rigid shell member is selected from a variety of sizes of rigid shell members having incremental sizing, in which the variety of incremental sizing corresponds to any standard system of shoe sizes.

7. An ankle-foot orthosis comprising:

a rigid shell member having an upper section, the upper section having a generally U-shaped cross-sectional configuration;

a lower shell section rigidly attached to and extending away from the upper section at less than a 90° angle, the lower section having a foot bed and a generally U-shaped cross-sectional configuration;

a removable wedge foot bed insert configured for placement on to the flat foot bed in the lower shell arm which when placed on the lower shell section when the lower shell section is at an angle of less than 90° to the upper shell section, presents a foot bed in which the medial side of the foot bed is higher than the lateral side of the foot bed, and the cross-section of the foot bed from one side to the other shows a top surface angle of greater than 00 inclusive of 15°.

8. An ankle-foot orthosis comprising:

a rigid shell member having an upper section, the upper section having a generally U-shaped cross-sectional configuration;

a lower shell section rigidly attached to and extending away from the upper section at an angle less than 90°, the lower section having a foot bed and a generally U-shaped cross-sectional configuration;

a removable wedge foot bed insert configured for placement on to the flat foot bed in the lower shell arm which when placed on the lower shell section when the lower shell section is at substantially a right angle to the upper shell section, presents a foot bed in which the medial side of the foot bed is lower than the lateral side of the foot bed, and the cross-section of the foot bed from one side to the other shows a top surface angle of greater than 00 inclusive of 15°.

9. A method for treating plantar faciitis comprising:

securing a rigid shell to the lower posterior portion of the leg and the foot, a rigid shell having an upper section and a lower section, both having generally U-shaped cross-sections, the lower section extending at an angle less than 90° from the upper section and having a generally flat foot bed portion, the upper section being configured to generally conform to the lower portion of a human leg, and the lower section being configured to receive a bottom surface of a foot attached to the leg; and inserting a removable wedge foot bed insert being inclined from a heel portion of the foot bed to a toe portion of the foot bed to thereby form an inclined foot bed which prevents plantarflexion, the rigid shell being secured to the leg and foot using a securing mechanism which is flexible in at least an area above the foot bed to allow for adjustable degrees of dorsiflexion while preventing plantarflexion past the inclined foot bed.

10. A method for treating plantar fasciitis comprising:

inserting a removable wedge into a foot bed portion of a rigid shell having an upper section and a lower section both having generally U-shaped cross-sections, the lower section extending at an angle less than 90° from the upper section and having a generally flat foot bed portion, the upper section being configured to generally conform to the lower portion of a human leg, and the lower section being configured to receive a bottom surface of a foot attached to the leg, the wedge being configured to receive a bottom surface of a foot attached to the leg, the wedge being inclined from a heel portion of the foot bed to a toe portion of the foot bed to a toe portion of the foot bed to thereby form an inclined foot bed which prevents plantar flexion; and securing the rigid shell to the lower posterior portion of leg and foot using a securing mechanism which is flexible in at least an area above the foot bed to allow for adjustable degrees of dorsiflexion while preventing plantarflexion past the inclined foot bed.

11. An orthosis comprising:

a rigid shell member with an inside surface and an outside surface, having an upper section and a lower section, both upper and lower sections having generally U-shaped cross-sections, the lower section having a heel portion and a toe portion, and extending at an angle of less than 90° from the upper section and having a generally flat foot bed portion, with the heel portion narrower than the toe portion and designed for close anatomical fit with a heel of a human patient, the upper section being configured for close and anatomically conforming shape to the lower posterior portion of a human leg, with a sagital concavity which conforms to the human leg and maintains the human heel in a floated position from the flat foot bed, and the upper section of a length which corresponds with the distance from the patient's heel to above the thickest portion of the gastroc-soleous muscle of the patient, the lower section being configured to receive a removable wedge foot bed insert, and the rigid shell member being shaped so that the rigid shell member defines an opening around a medial and a lateral prominence of a human ankle;

a removable wedge foot bed insert, being shaped and sized to be received in the foot bed portion, the wedge being inclined from a heel portion of the foot bed to a toe portion of the foot bed to thereby form an inclined foot bed which prevents plantarflexion, and the removable wedge foot bed insert having a cushioning top surface and being made of a semi-rigid material;

a soft jacket which covers the inside and outside surfaces of the rigid shell member, and to which is attached a securing means; and a means of securing the rigid shell to the lower posterior portion of the leg and foot, the securing mechanism being flexible in at least an area above the foot bed to allow for adjustable degrees of dorsiflexion while preventing plantarflexion past the inclined foot bed.

12. The orthosis of claim 11, wherein the lower shell section is at an angle of less than 90° to the upper shell section, and the removable foot wedge insert results in a foot bed which is less than 90° in relation to the upper shell section.

13. The orthosis of claim 11, wherein the lower shell section is at an angle of less than 90° to the upper shell section and the removable wedge foot bed insert results in a foot bed which is 85° in relation to the upper shell section.

14. The orthosis of claim 11, wherein the lower shell section is at an angle of less than 90° to the upper shell section and the removable wedge foot bed insert results in a foot bed which is 80° in relation to the upper shell section.

15. The orthosis of claim 11, wherein the lower shell section is at an angle of less than 90° in relation to the upper shell section and the removable wedge foot bed insert results in a foot bed which may vary from less than 90° to 75° in relation to the upper shell section.

16. The orthosis of claim 11, which further comprises a stabilizing cradle to which one or two orthosis can be attached, and which immobilizes said orthoses.

17. A method for treating plantar faciitis in a human patient comprising:

inserting a removable wedge into a foot bed portion of a rigid shell having an upper section and a lower section, both sections having generally U-shaped cross-sections, the lower section having a heel portion and a toe portion, the heel portion being narrower than the toe portion for close anatomical fit to a human foot, and extending at an angle of less than 90° from the upper section and having a generally flat foot bed portion, the upper section being configured for close anatomical conformance to the lower portion of a human leg, and when worn by a patient to extend from a heel of the patient to above the thickest part of a patient's gastrocsoleus muscle, and the lower section being configured to receive a bottom surface of a foot attached to the leg, the rigid shell being covered with a soft covering on its inside and outside surface, the wedge being configured to receive a bottom surface of a foot attached to the leg, the wedge being inclined from a heel portion of the foot bed to a toe portion of the foot bed to a toe portion of the foot bed to thereby form an inclined foot bed which prevents plantar flexion;

securing the rigid shell to the lower posterior portion of a leg and foot using a securing mechanism which is flexible in at least an area above the foot bed to allow for adjustable degrees of dorsiflexion while preventing plantarflexion past the inclined foot bed; and requiring the patient to wear the rigid shell, the soft covering, and the wedge, secured by the securing mechanism to the lower posterior portion of the leg and the foot, while in a reclining position.

18. A method for preventing hip movement in a human patient comprising:

securing the rigid shell having an inner and outer surface and an upper section and a lower section, both sections having generally U-shaped cross-sections, the lower section having a heel portion and a toe portion, the heel portion being narrower than the toe portion for close anatomical fit to a human foot, and extending at an angle of less than 90° from the upper section and having a generally flat foot bed portion, the upper section being configured for close anatomical conformance to the lower portion of a human leg, and when worn by a patient to extend from a heel of the patient to above the thickest part of a patient's gastrocsoleus muscle, and the lower section being configured to receive a bottom surface of a foot attached to the leg, the rigid shell being covered with a soft covering on its inside surface;

securing the rigid shell to the lower posterior portion of leg and foot of a human patient using a securing mechanism which is flexible in at least an area above the foot bed to allow for adjustable degrees of dorsiflexion while preventing plantarflexion past the inclined foot bed;

placing the rigid shell with the leg and foot of the patient in a stabilizing cradle and securing the rigid shell in a fixed position in the stabilizing cradle with a means of attachment; and requiring the patient to wear the rigid shell, the soft covering, secured by the securing mechanism to the lower posterior portion of the leg and the foot, and the rigid shell attached to the stabilizing cradle with a means of attachment while in a reclining position.

\* \* \* \* \*